United States Patent [19]

Zipperer et al.

[11] Patent Number: 4,939,157
[45] Date of Patent: Jul. 3, 1990

[54] PYRIDINE-N-OXIDES AND FUNGICIDAL COMPOSITIONS CONTAINING SAME AND FUNGICAL USE

[75] Inventors: Bernhard Zipperer, Dirmstein; Ernst Buschmann, Ludwigshafen; Manfred Lauer, Ludwigshafen; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 292,439

[22] Filed: Dec. 30, 1988

[30] Foreign Application Priority Data

Dec. 31, 1987 [DE] Fed. Rep. of Germany ....... 3744620

[51] Int. Cl.$^5$ .................... C07D 213/89; A01N 43/40
[52] U.S. Cl. ...................................... 514/277; 546/344
[58] Field of Search .......................... 546/344; 514/277

[56] References Cited

U.S. PATENT DOCUMENTS 3,396,224  8/1968  Van Heyningen ................. 514/277

Primary Examiner—Alan L. Rotman
Attorney, Agent, or Firm—Oblon, Spivak, McClelland, Maier & Neustadt

[57] ABSTRACT

Substituted pyridine-N-oxides of the formula

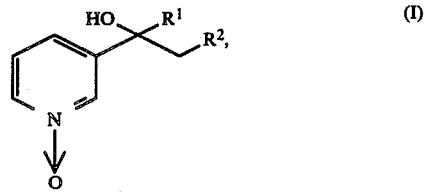

where $R^1$ is alkyl and $R^2$ is phenyl or substituted phenyl, salts thereof which are physiologically tolerated by plants, and fungicides containing them.

5 Claims, No Drawings

PYRIDINE-N-OXIDES AND FUNGICIDAL COMPOSITIONS CONTAINING SAME AND FUNGICAL USE

The present invention relates to novel pyridine-N-oxides and salts thereof, fungicidal agents containing these compounds, and methods of preparing them.

It has been disclosed (EP No. 69,330) to use 3-pyridylmethanols as fungicides. However, their fungicidal action is only satisfactory at high application rates.

We have now found that novel pyridine-N-oxides of the formula

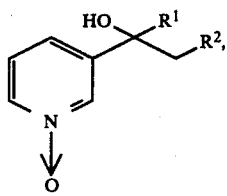

where $R^1$ is $C_1$-$C_{12}$-alkyl, and $R^2$ is phenyl or substituted phenyl bearing from one to three radicals selected from the group consisting of $C_1$-$C_4$-alkyl, $C_1$-$C_4$-haloalkyl, $C_1$-$C_4$-alkoxy, $C_1$-$C_4$-haloalkoxy and halogen, and their salts physiologically tolerated by plants, have a better fungicidal action than the prior art 3-pyridylmethanols and are also much better tolerated by plants.

$R^1$ is $C_1$-$C_{12}$-alkyl, and especially $C_3$-$C_8$-alkyl, for example methyl, ethyl, n-propyl, isopropyl, n-butyl, isobutyl, tert-butyl, n-pentyl, isopentyl, neopentyl, n-hexyl, neohexyl, n-heptyl, n-octyl, n-nonyl, n-decyl, n-undecyl and n-dodecyl.

$R^2$ is for example phenyl, mono-, di- or trimethylphenyl, isopropylphenyl, tert-butylphenyl, trifluoromethylphenyl, pentafluoroethylphenyl, mono-, di- or trimethoxyphenyl, tert-butoxyphenyl, tetrafluoroethoxyphenyl, fluorophenyl, chlorofluorophenyl, and mono-, di- or trichlorophenyl.

Examples of salts are acid addition salts, for instance salts of inorganic acids, e.g., hydrochloric acid, hydrobromic acid, sulfuric acid and phosphoric acid, or of organic acids, e.g., $C_1$-$C_4$-alkylcarboxylic acids, acetic acid, propionic acid, tolylsulfonic acid and dodecylbenzenesulfonic acid.

The compounds contain at least one asymmetrical carbon atom, and therefore appear in the form of their optical isomers, viz., enantiomers. The present invention embraces both the pure enantiomers and the racemates and diastereomers.

The pyridine-N-oxides of the formula I may be produced for example by oxidizing, in conventional manner, a 3-substituted pyridine of the formula (II)

where $R^1$ and $R^2$ have the above meanings. Examples of suitable oxidants are peracids, or peracids formed in situ from hydrogen peroxide and carboxylic anhydrides, hydrogen peroxide or organic derivatives of hydrogen peroxide (cf., for example, R. A. Abramovitch and E. M. Smith, Chemistry of Heterocyclic Compounds, vol. 14, Suppl. 2, p. 1 et seq., John Wiley, New York, 1974; A. R. Katritzky, J. M. Lagowski, The Chemistry of Heterocyclic N-Oxides, p. 21 et seq., Academic Press, New York, 1971). A particularly advantageous oxidant for this process is 3-chloroperbenzoic acid (cf. J. C. Craig, K. K. Purnshothaman, J. Org. Chem., 35, 1721, 1970). Examples of diluents when the oxidation is carried out with 3-chloroperbenzoic acid are chlorohydrocarbons, especially dichloromethane and trichloromethane.

3-Pyridylcarbinols of the formula II are known from EP-A No. 69,330. The manufacturing instructions given there can be applied without any difficulty to other alkyl and aryl radicals.

The preparation of the novel pyridine-N-oxides is illustrated by the following examples.

EXAMPLE 1

1-(2,4-Dichlorophenyl)-2-(pyridine-1-oxide-3-yl)-2-decanol

While stirring, a solution of 7.6 g (0.044 mol) of 3-chloroperbenzoic acid in 60 ml of dichloromethane is dripped into a solution of 8.5 g (0.022 mol) of 1-(2,4-dichlorophenyl)-2-(pyridin-3-yl)-2-decanol in 100 ml of dichloromethane. After the reaction solution has been stirred overnight, it is washed twice with 5 wt % strength sodium hydroxide solution and once with water, dried over sodium sulfate and evaporated down under reduced pressure. The oily residue is stirred with diisopropyl ether until crystallization occurs. After suction filtration and drying under reduced pressure, there is obtained 6.8 g (78% of theory) of a beige-colored powder having a melting point of 99°–102° C. (compound no. 1).

EXAMPLE 2

1-(4-Fluorophenyl)-2-(pyridine-1-oxide-3-yl)-2-decanol

While stirring, a solution of 7.6 g (0.044 mol) of 3-chloroperbenzoic acid in 60 ml of dichloromethane is dripped into a solution of 7.5 g (0.022 mol) of 1-(2,4-dichlorophenyl)-2-(pyridin-3-yl)-2-decanol in 100 ml of dichloromethane. After the reaction solution has been stirred overnight, it is concentrated to about half of its volume and introduced into a column containing about 300 g of basic aluminum oxide (activity stage I). Nonpolar impurities are eluted with dichloromethane, and the pyridine-1-oxide with dichloromethane/methanol (3:1). Concentration under reduced pressure gives 5.5 g (70% of theory) of compound no. 2 as a yellow oil. $^1$H-NMR of the pyridine moiety (200 MHz, CDCl$_3$): $\delta=8.30$ (2-H), 8.05 (6-H), 7.20 (4-H, 5-H).

The following compounds may be prepared analogously:

TABLE 1

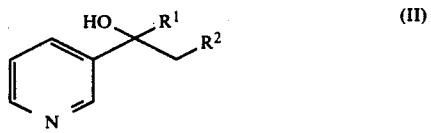

| Com. pound No. | $R^1$ | $R^2$ | mp (°C.) |
|---|---|---|---|
| 1 | n-octyl | 2,4-dichlorophenyl | 99–102 |

TABLE 1-continued

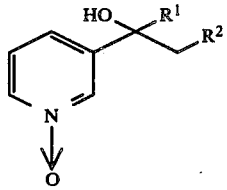

| | | | |
|---|---|---|---|
| 2 | n-octyl | 4-fluorophenyl | oil |
| 3 | isopropyl | 4-chlorophenyl | |
| 4 | isopropyl | 2-chlorophenyl | |
| 5 | isopropyl | 2,4-dichlorophenyl | 150-151 |
| 6 | n-Propyl | 2,4-Dichlorphenyl | |
| 7 | n-Propyl | Phenyl | |
| 8 | n-Propyl | 4-Methylphenyl | |
| 9 | n-Butyl | 2,4-Dichlorphenyl | |
| 10 | n-butyl | 4-chlorophenyl | |
| 11 | isobutyl | 2,4-dichlorophenyl | 161 |
| 12 | isobutyl | 4-chlorophenyl | |
| 13 | isobutyl | 4-fluorophenyl | |
| 14 | isobutyl | 3-trifluoromethylphenyl | |
| 15 | isobutyl | 2-chlorophenyl | |
| 16 | n-pentyl | 4-chlorophenyl | |
| 17 | n-pentyl | 2,4-dichlorophenyl | |
| 18 | n-pentyl | 2-chlorophenyl | |
| 19 | neo-hexyl | 2-chlorophenyl | |
| 20 | neo-hexyl | 4-chlorophenyl | |
| 21 | neo-hexyl | 2,4-dichlorophenyl | 150-153 |
| 22 | neo-hexyl | 4-trifluoromethylphenyl | |
| 23 | neo-hexyl | 3-trifluoromethylphenyl | |
| 24 | neo-hexyl | 4-fluorophenyl | |
| 25 | neo-hexyl | 4-tert-butylphenyl | |
| 26 | neo-hexyl | 4-chloro-3-trifluoromethylphenyl | |
| 27 | n-hexyl | 2,4-dichlorophenyl | |
| 28 | n-heptyl | 2,4-dichlorophenyl | |
| 29 | n-octyl | 2-chlorophenyl | 65-67 |
| 30 | n-octyl | 4-chlorophenyl | oil |
| 31 | n-octyl | 3-trifluoromethylphenyl | oil |
| 32 | n-nonyl | 2,4-dichlorophenyl | |
| 33 | n-decyl | 2,4-dichlorophenyl | |
| 34 | n-undecyl | 2,4-dichlorophenyl | |
| 35 | n-dodecyl | 2,4-dichlorophenyl | |
| 36 | n-dodecyl | 4-chlorophenyl | |
| 37 | n-dodecyl | 2-chlorophenyl | 57-64 |
| 38 | n-dodecyl | 4-fluorophenyl | 73-76 |
| 39 | neo-pentyl | 2,4-dichlorophenyl | |
| 40 | neo-pentyl | 4-chlorophenyl | |
| 41 | neo-pentyl | 2-chlorophenyl | |
| 42 | neo-pentyl | 4-fluorophenyl | |
| 43 | neo-pentyl | 2-fluorophenyl | |
| 44 | neo-pentyl | 4-trifluoromethylphenyl | |
| 45 | neo-pentyl | 3-trifluoromethylphenyl | |
| 46 | neo-pentyl | 4-(4-tert-butylphenyl) | |

| Compound No. | NMR data and IR values |
|---|---|
| 2 | $^1$H-NMR (CDCl$_3$): δ = 8.30 (s, 2'-H), 8.05 (s, 6'-H), 7.20 (br.m, 4'-H, 5'-H), 7.10 (dd, 2H$_o$), 6.85 (dd, 2H$_m$), 4.75 (br.s, OH), 3.03 (dd, 1-CH$_2$), 1.80 (br.m, 3-CH$_2$), 1.20 (br.m, 4-bis 9-CH$_2$), 0.85 (t, 10-CH$_3$). IR (film): ν = 2953, 2927, 2855, 1601, 1509, 1426, 1298, 1261, 1223, 1158, 1015 cm$^{-1}$. |
| 30 | $^1$H-NMR (CDCl$_3$): δ = 8.30 (s, 2'-H), 8.05 (s, 6'-H), 7.20 (br.m, 4'-H, 5'-H), 7.15 (d, 2H$_o$), 6.95 (d, 2H$_m$), 4.25 (br.s, OH), 3.00 (dd, 1-CH$_2$), 1.78 (br.m, 3-CH$_2$), 1.20 (br.m, 4-bis 9-CH$_2$), 0.85 (t, 10-CH$_3$). IR (film): ν = 3223, 2927, 2854, 1602, 1490, 1467, 1428, 1258, 1149, 1093, 1016 cm$^{-1}$. |
| 31 | $^1$H-NMR (CDCl$_3$): δ = 8.30 (s, 2'-H), 8.05 (s, 6'-H), 7.40 bis 7.15 (m, 4'-H, 5'-H, 2H$_o$, H$_m$, H$_p$), 4.65 (br.s, OH), 3.10 (dd, 1-CH$_2$), 1.80 (br.m, 3-CH$_2$), 1.20 (br.m, 4- to 9-CH$_2$), 0.85 (t, 10-CH$_3$). IR (film): ν = 3220, 2928, 2856, 1602, 1428, 1333, 1259, 1204, 1163, 1124, 1096, 1075 cm$^{-1}$. |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaequalis* (scab) in apples,
*Helminthosporium* species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium* and *Verticillium* species in various plants,
*Plasmopara viticola* in grapes,
*Alternaria* species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 5 is mixed with 10 parts by weight of N-methyl-α-pyrrolidone. A mixture is obtained which is suitable for application in the form of very fine drops.

II. 20 parts by weight of compound no. 5 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 5 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 5 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 5 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 5 is intimately mixed with 97 parts by weight of particulate kaolin. A dust is obtained containing 3% by weight of the active ingredient.

VII. 30 parts by weight of compound no. 5 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 5 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 5 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum. The following list of fungicides with which the novel compounds may be combined is intended to illustrate possible combinations but not to impose any restrictions.

Examples of fungicides which may be combined with the novel compounds are:
sulfur,
 dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
 nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
 heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide), 1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

In the use example below, 1-(2,4-dichlorophenyl)-2-(pyridin-3-yl)-3-methyl-2-butanol (A) disclosed in EP No. 69,330 was used as comparative agent.

USE EXAMPLE

Action on *Botrytis cinerea*

In the open, small plots of strawberry plants of the Senga-Sengana variety were sprayed to runoff in the main blossom period with an aqueous suspension consisting (dry basis) of 80 wt % of active ingredient and 20% of dispersant. After two days, all the plots were inoculated with a spore suspension of Botrytis cinerea. This treatment was repeated after a further 5 days. 38 days later, the ripe fruit was checked for Botrytis attack.

The results show that active ingredient 5, applied at a rate of 2 kg/ha, had a better fungicidal action (75%) than prior art active ingredient A (18%).

We claim:

1. A 3-substituted pyridine-N-oxide of the formula

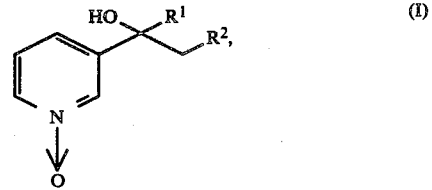

where $R^1$ is $C_1$-$C_{12}$-alkyl, and $R^2$ is phenyl or substituted phenyl bearing from one to three radicals selected from the group consisting of $C_1$-$C_4$-alkyl, $C_1$-$C_4$-haloalkyl, $C_1$-$C_4$-alkoxy, $C_1$-$C_4$-haloalkoxy and halogen, and its salts physiologically tolerated by plants.

2. A fungicidal agent containing an inert carrier and a 3-substituted pyridine-N-oxide of the formula

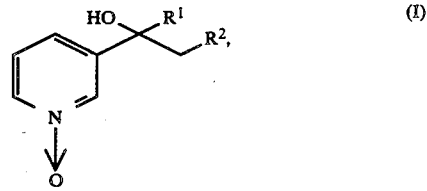

where $R^1$ is $C_1$-$C_{12}$-alkyl, and $R^2$ is phenyl or substituted phenyl bearing from one to three radicals selected from the group consisting of $C_1$-$C_4$-alkyl, $C_1$-$C_4$-haloalkyl, $C_1$-$C_4$-alkoxy, $C_1$-$C_4$-haloalkoxy and halogen, or a salt thereof physiologically tolerated by plants.

3. A process for combating fungi, wherein the fungi or the materials, plants, soils or seeds threatened by fungus attack are treated with a fungicidally effective amount of a 3-substituted pyridine-N-oxide of the formula

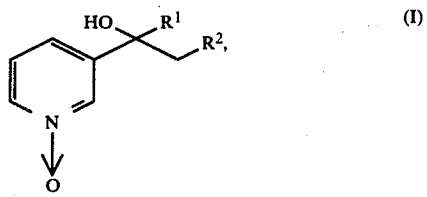

where $R^1$ is $C_1$-$C_{12}$-alkyl, and $R^2$ is phenyl or substituted phenyl bearing from one to three radicals selected from the group consisting of $C_1$-$C_4$-alkyl, $C_1$-$C_4$-haloalkyl, $C_1$-$C_4$-alkoxy, $C_1$-$C_4$-haloalkoxy and halogen, or a salt thereof physiologically tolerated by plants.

4. A compound as set forth in claim 1, where $R^1$ is isopropyl and $R^2$ is 2,4-dichlorophenyl.

5. A compound as set forth in claim 1, where $R^1$ is isobutyl and $R^2$ is 2,4-dichlorophenyl.

* * * * *